United States Patent [19]

Takaki

[11] Patent Number: 5,711,291
[45] Date of Patent: Jan. 27, 1998

[54] BLOOD PRESSURE TRANSDUCER

[75] Inventor: Sunsuke Takaki, Sagamihara, Japan

[73] Assignee: Minnesota Mining and Manufacturing Company, St. Paul, Minn.

[21] Appl. No.: 351,323
[22] PCT Filed: Jun. 18, 1993
[86] PCT No.: PCT/US93/06105
  § 371 Date: Dec. 12, 1994
  § 102(e) Date: Dec. 12, 1994
[87] PCT Pub. No.: WO94/00051
  PCT Pub. Date: Jan. 6, 1994

[30] Foreign Application Priority Data

Jun. 29, 1992 [JP] Japan ................................. 4-170949
Jun. 1, 1993 [JP] Japan ................................. 5-130516

[51] Int. Cl.⁶ ................................................. A61B 5/00
[52] U.S. Cl. ........................... 128/667; 128/673; 128/687; 250/227.014
[58] Field of Search .............. 250/231.19, 227.17, 250/227.14, 227.16, 227.22; 73/708; 128/634, 664–7, 672–5, 687, 748

[56] References Cited

U.S. PATENT DOCUMENTS

| 4,711,246 | 12/1987 | Alderson | 128/667 |
|---|---|---|---|
| 4,750,796 | 6/1988 | Shibata et al. | 250/227.14 |
| 4,915,473 | 4/1990 | Haese et al. | 250/227.14 |
| 4,924,877 | 5/1990 | Brooks | 128/667 |
| 5,018,529 | 5/1991 | Tenerz et al. | 128/667 |
| 5,089,697 | 2/1992 | Prohaska | 250/227.14 |
| 5,138,152 | 8/1992 | Botting | 250/227.16 |
| 5,195,375 | 3/1993 | Tenerz et al. | 128/667 |
| 5,260,566 | 11/1993 | Reed | 250/227.16 |
| 5,517,998 | 5/1996 | Madison | 128/667 |

FOREIGN PATENT DOCUMENTS

| 0 392 897 | 10/1990 | European Pat. Off. . |
|---|---|---|
| 1001809 | 8/1965 | United Kingdom . |

OTHER PUBLICATIONS

"Fiber–optic Pressure Transducer for Use Near MR Magnetic Fields", Carlton R. Roos and Frank E. Carroll, Jr., *Radiology*, vol. 156, No. 2, p. 548.
PCT Search Report for PCT/US93/06105.

*Primary Examiner*—Robert L. Nasser
*Attorney, Agent, or Firm*—F. Andrew Ubel

[57] ABSTRACT

This invention relates to a blood pressure transducer (8) and provides a safe and economical transducer by providing a novel optical fiber (80) made of a transparent elastomer. The present invention provides an invasive direct blood pressure transducer (8) of an external sensor system consisting of a catheter (1a), a pressure tub (6) connected to the catheter at one of the ends thereof and a pressure transducer (8) connected to the other end of the pressure tube (6), part of the pressure transducer is composed of an optical fiber (80) made of a transparent elastomer.

19 Claims, 4 Drawing Sheets

BLOOD PRESSURE TRANSDUCER

FIELD OF THE INVENTION

This invention relates to a blood pressure transducer in medical measuring instruments.

BACKGROUND OF THE INVENTION

Invasive direct blood pressure measurement is often performed on patients in the intensive care unit or the coronary care unit of a hospital, during heart surgery, and so forth. This method can observe the blood pressure waveform with a higher level of accuracy than a non-invasive indirect blood pressure transducer, and can also measure a local pressure such as an internal pressure of the heart. The following three systems have been employed for this purpose and are examples of invasive direct blood pressure transducers. FIGS. 10 and 11, discussed below, are explanatory views of conventional systems. Hereinafter, these three systems and their drawbacks will be explained.

(1) External Sensor System Using Semiconductor Pressure Transducer:

This first system is illustrated in FIG. 10 and is the most widely used type at present. The transducers of this type have been put on the market by a large number of manufacturers. A catheter 1 filled with a physiological saline solution through a pressure tube 2 is inserted into a blood vessel of the arm of a patient, and the other end of the pressure tube 2 is connected to a semiconductor pressure transducer 3. This transducer 3 detects the change of the pressure of the saline solution, and a monitor 4 observes the change of the blood pressure.

This system is convenient and can accurately measure a patient's blood pressure for an extended period of time. Since many of the transducers are of a disposable type, there is a less danger of infection to others. Nonetheless, since the semiconductor pressure transducer 3 is of an electrical type, there is the danger of electric shock to the patient due to the failure of the apparatus, and the like. Furthermore, since the semiconductor pressure transducers 3 are complicated in structure, the problem of the high production cost is left unsolved when using them as a disposable device.

(2) Sensor System Using Catheter with Semiconductor Pressure Transducer at its tip:

This second system is shown in FIG. 11. A small semiconductor pressure transducer 5 is assembled into the tip of a catheter 1, and the pressure of a local portion (e.g. internal chamber of the heart, large blood vessels, etc) is observed by a monitor unit 4 by inserting the catheter 1 into the blood vessel or chamber. The physiological saline solution is charged into a pressure tube 2 in the same way as in the first system. This system, too, has already been put on the market.

According to this system, however, it is difficult to produce a probe having as small a diameter as the catheter 1. Furthermore, this system is not suitable for taking measurements over a prolonged time, e.g., by leaving the probe inside a small blood vessel. Finally, the danger of electric shock to the patient is even greater than in the first system described above.

(3) Sensor System Using Catheter with Optical Fiber:

This third system has the same basic structure as the second system. However, to eliminate the potential problem of electric shock inherent in the second system, this system uses a sensor comprising the combination of an optical fiber and a diaphragm, etc, in place of the semiconductor pressure sensor 5 (see KOKAI Japanese Unexamined Patent Publication No. 62-47335).

While the problem of harmful electric shock can be avoided by using this optical system, other problems remain. For example, additional components such as a diaphragm, etc., become necessary, therefore, the sensor becomes larger. This system is also unsuitable for taking measurements over a prolonged time.

SUMMARY OF THE INVENTION

The present invention provides a blood pressure transducer. The blood pressure transducer according to the present invention uses an optical fiber made of a transparent elastomer as the pressure transducer, and provides an economical, disposable structure which is safe due to its reduced potential to cause an undesirable electric shock. The transducers of the present invention are capable of continuously measuring arterial and venous pressures over a prolonged period of time and can easily be calibrated.

DETAILED DESCRIPTION OF THE INVENTION

In view of the problems described above in the background section, the present invention provides a blood pressure transducer which is capable of continuously measuring the arterial and venous pressures by means of a pressure transducer through a catheter, and which eliminates the danger of electric shock. The transducer is small in size, can be calibrated easily, and is economical and disposable. The transducer comprises an optical fiber made of a transparent elastomer as a pressure transducer.

The present invention provides an invasive direct blood pressure transducer of an external sensor type comprising a pressure tube connected to one of the ends of a catheter and a pressure transducer connected to the other end of the pressure tube. The invasive direct blood pressure transducer according to the present invention is characterized in that a part of the pressure transducer is composed of an optical fiber made of a transparent elastomer, and wherein the pressure transducer is equipped with a light source at one of the ends thereof and with an optical sensor at the other end.

Figure 2:
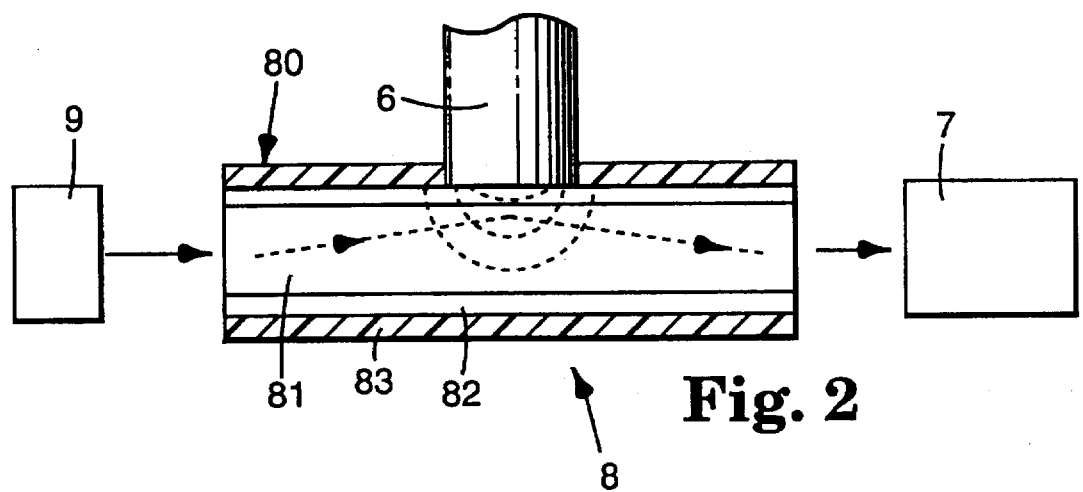
FIG. 2 is an explanatory view useful for explaining the operation principle of the present invention.

In a preferred embodiment, the pressure transducer is equipped with a light source at one of the ends thereof and with an optical sensor at the other end thereof, the pressure tube is connected to the optical fiber at an intermediate part of the optical fiber, light is allowed to be incident from the light source, and, as shown by dotted lines in FIG. 2, the optical sensor detects the change of a light intensity of the incident light resulting from the change of a transmission factor of the optical fiber in response to the change of an internal pressure of a blood vessel.

Further, in another embodiment, the pressure transducer is equipped with a sensitivity adjustment screw for adjusting variance of sensitivity of said optical fiber.

Still further, in another embodiment, the pressure transducer is equipped with a light measuring unit including a light source, an optical sensor and a light splitter at one of the ends thereof and with a reflection unit at the other end thereof for reflecting a light from the light source, the pressure tube is connected to the optical fiber at an intermediate part of the optical fiber, the light is allowed to be incident from the light source through the light splitter, and the optical sensor detects the change of a light intensity of a reflection light reflected by the reflection unit resulting from the change of a transmission factor of the optical fiber in response to the change of an internal pressure of a blood vessel.

Figure 1:
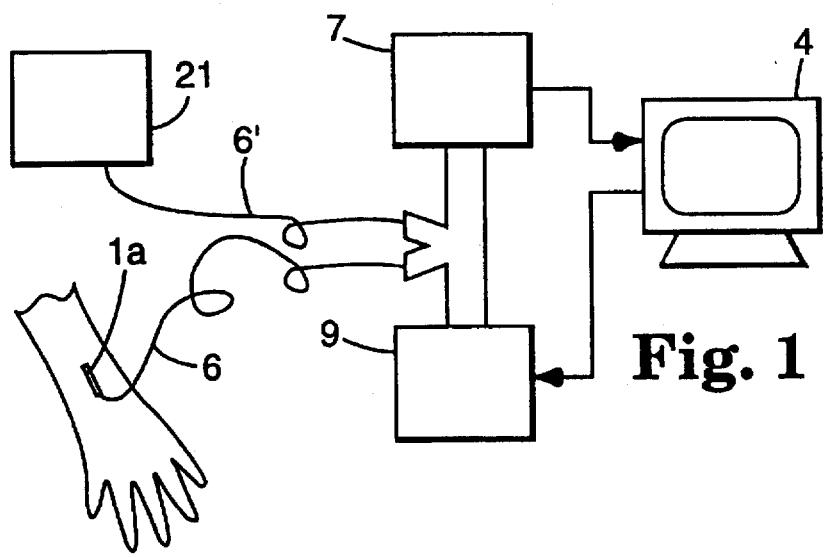
FIG. 1 is a structural view of principal portions of an invasive direct blood pressure transducer according to the present invention.
Figure 8:
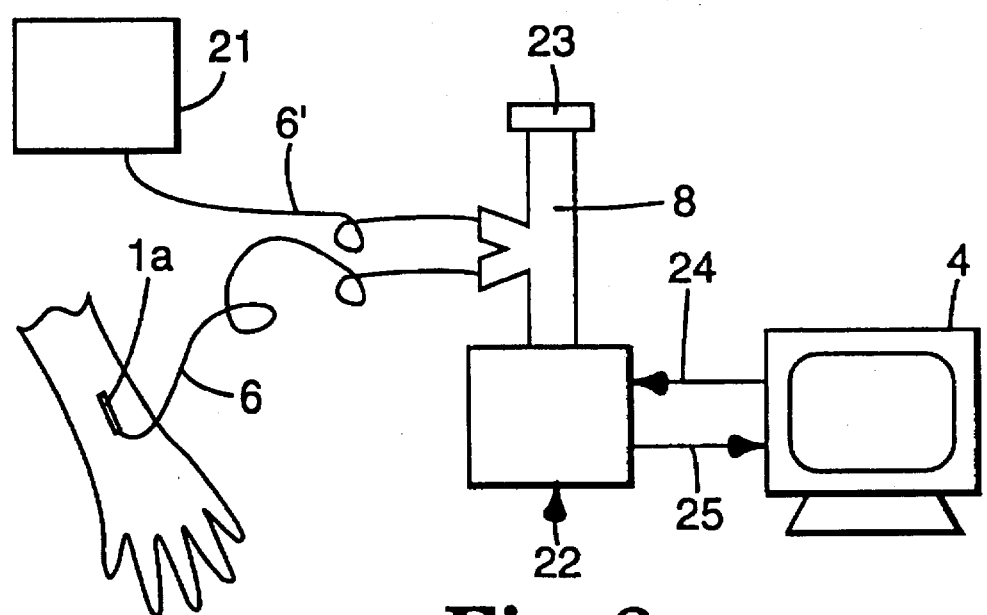
FIG. 8 is a structural view of an invasive direct blood pressure transducer according to another embodiment of the present invention.

As described above, the present invention provides two systems for detecting the change of an amount of light caused by the change of ,the blood pressure, i.e., one system utilizing a transmission light as shown in FIG. 1, and the other system utilizing a reflected light as shown in FIG. 8.

FIG. 1 is a structural view of the principal portions of an invasive direct blood pressure transducer according to the present invention. As shown in the drawing, the invasive direct blood pressure transducer according to the present invention comprises a pressure transducer 8, a light source 9, an optical sensor 7, a monitor unit 4, a tube 6 and 6' (optionally comprising a vinyl polymer), and a catheter 1a. The transducer according to the present invention uses an optical blood pressure transducer 8 comprising an optical fiber made of a transparent elastomer.

A liquid such as a physiological saline solution is packed into the pressure receiving portion of the pressure transducer 8, the tube 6 and the catheter 1a. The pressure of this solution changes with the change of the pressure of a blood vessel, so that the internal pressure of the blood vessel can be transmitted to the pressure transducer 8.

FIG. 2 is an explanatory view useful for explaining the principle of operation of the present invention. The optical fiber 80, made of a transparent elastomer, used for the pressure transducer of the present invention exhibits the following operation. The optical fiber 80 comprises a core portion 81 made of a transparent elastomer having a high refractive index, a cladding portion 82 made of a transparent elastomer having a low refractive index and a jacket portion 83 made of an opaque (e.g., black) elastomer which serves to prevent the introduction of any external light into the sensor. When light is allowed to be incident into one of the ends of the optical fiber 80 from the light source 9, the light undergoes total reflection on the boundary between the core 81 and the cladding 82 and exits the other end of the optical fiber 80.

When the internal pressure of the blood vessel acts on part of the side surface of this optical fiber 80 through the physiological saline solution packed into the tube 6, the inside of the optical fiber 80 receiving this pressure undergoes deformation as represented by dotted line, and the boundary between the core 81 and the cladding 82 is disturbed, so that the intensity of the outgoing light drops. On the other hand, since the optical fiber 80 is made of an elastomer it returns to its original state unless the pressure is maintained thereto, and the light intensity returns to the original level, as well. The change of the light intensity in this instance is detected by the optical sensor 7 receiving the outgoing light, and the monitor unit 4 observes this change so as to measure the blood pressure.

Suitable elastomers for use in the present invention as the transparent elastomer for the optical fiber 80 include: silicone elastomers, acrylate elastomers, fluorocarbon elastomers, vinyl chloride elastomers, ethylene propylene elastomers, etc. After the core portion is molded from these materials by, for example, a known extrusion molding method or casting method, the cladding portion and the jacket portion are molded by a coating method.

Known light emitting diodes, laser, xenon lamps, halogen lamps, etc, can be used as the light source 9. Known devices such as photo-diodes, photomultipliers, etc, can be used as the optical sensor 7.

Figure 3:
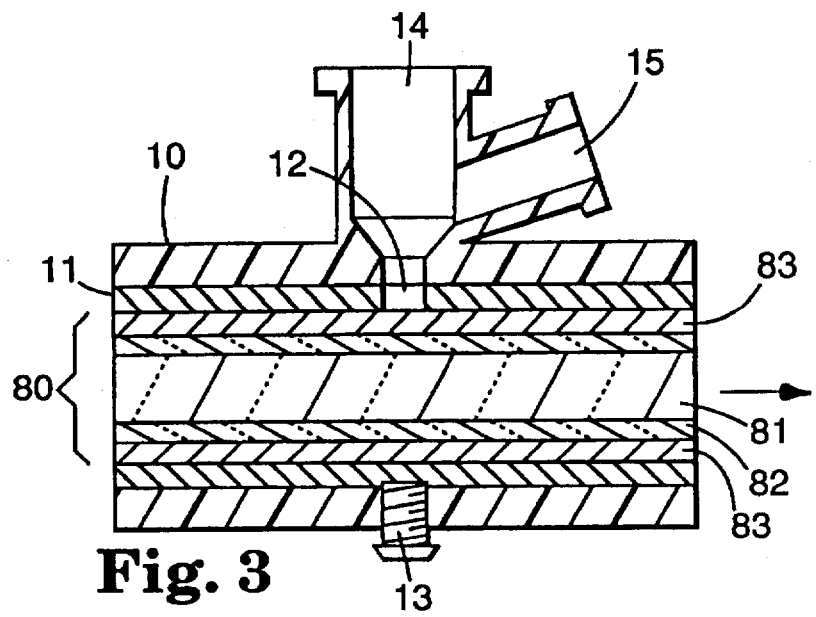
FIG. 3 is a detailed structural view of a pressure transducer according to the present invention.

FIG. 3 is a detailed structural view of the transducer portion of the present invention. The optical fiber 80 is disposed in a cell 10 and is held in place by packing a packing material 11 which fixes the optical fiber to the cell at sites other than the site of a pressure sensitive hole 12. A sensitivity adjustment screw 13 is fitted to the cell immediately below, and opposite to, the pressure sensitive hole 12. When this screw 13 is turned up and down, a pressure can be applied to the core 81 and the cladding 82 through the jacket portion 83, and the sensitivity can be adjusted by intentionally causing deformation of the optical fiber 80 by this externally applied pressure. In other words, variance of the sensitivity of a plurality of pressure transducers can be calibrated to a predetermined sensitivity by turning up and down this screw 13. Reference numeral 14 denotes a flange portion for connecting the tube 6 and reference numeral 15 denotes the flange portion for connecting the vinyl tube 6', which connects the flash bag 21, through a valve 16.

Suitable materials for the cell 10 include polymeric materials such as polycarbonate, acrylate resin, epoxy resin, polyethylene, polypropylene, polystyrene, fluororesin, etc. Alternately, one may use a suitable metal or ceramic material to form the cell. If desired, one may optionally employ an opaque material (i.e., opaque to the wavelength of light being transmitted from the light source) for the cell. In such a case, the opaque elastomeric jacket 83 may be omitted. In general, however, transparent materials are preferred for use as the cell so that the operator may check visually for occurrence of air bubbles in the vicinity of the pressure sensitive hole 12. Suitable packing materials 11 for fixing the optical fiber include materials such as silicone resin, acrylate resin, fluororesin, urethane resin, vinyl chloride, ethylene-propylene resin, etc. A plastic screw or metallic screw can be used for the sensitivity adjustment screw 13.

Figure 4:
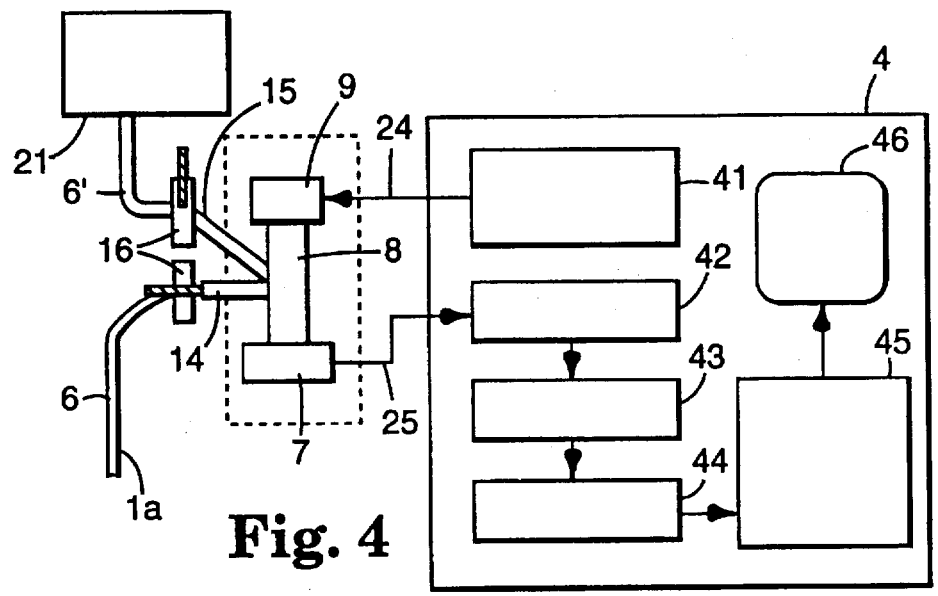
FIG. 4 is an overall structural view of the invasive direct blood pressure transducer according to the present invention.

FIG. 4 is an overall structural view of the invasive direct blood pressure transducer according to the present invention. To calibrate the invasive direct blood pressure transducer of the present invention, sensitivity adjustment of the pressure transducer 8 and sensitivity adjustment of the monitor unit 4 are necessary. The sensitivity of the pressure transducers 8 immediately after their production is mutually different due to a fine difference of structure inside the cell 10. Therefore, the sensitivity is adjusted to substantially an equal level by means of the sensitivity adjustment screw 13 of each pressure transducer 8. The pressure transducers 8 are preserved after sterilization, and are fitted to the monitor unit 4 when they are used. At this time, the intensity of light transmission through the optical fiber 80 is generally different from that of the initial calibration depending on factors such as the fitting positions of the light source 9 and the optical sensor 7. To compensate for these differences, the intensity of the light source 9 may be adjusted so that the intensity of the transmitted light becomes standardized at an arbitrary pressure (generally, at 0 mmHg). To standardize the base line of calibration, an auto-zero circuit which compulsorily makes the output signal zero is operated when the transducer is maintained at a pressure of 0 mmHg. Next, the light intensity of the light source 9 is adjusted in such a way that the intensity of the transmission light is standardized at a known valve when the transducer is maintained at a pressure of 200 mmHg. In this way, each pressure transducer can be calibrated easily.

In the monitor unit 4, reference numeral 41 denotes a stabilization unit for stabilizing fight power of the fight source 9; 42 is an amplifier for converting the light intensity detected by the optical sensor to a voltage and amplifying the voltage; 43 is a filter for picking up only those frequencies necessary for the measurement; 44 is a convertor for converting the voltage obtained by the filter 43 to a digital value; 45 is a micro-processor for converting the digital voltage value obtained by the convertor 44 to an actual blood pressure value; and 46 is a display unit for displaying the result of the microprocessor 45.

An example of each constituent component will now be explained in further detail. The following examples are offered to aid in the understanding of the present invention and are not to be construed as limiting the scope thereof.

EXAMPLES

Example 1

Fabrication of an Optical Fiber

A transparent silicone elastomer of a two-liquid RTV type (Sylgard™ 184, available from Dow Corning, Midland, Mich.) and having a refractive index of 1.430 was sufficiently mixed and then defoamed. The elastomer was charged into a vinyl chloride tube having an inner diameter of 1 mm and was cured at 65° C. for 4 hours. Thereafter, the robe was put into tetrahydrofuran and dissolved to provide a core of the silicone elastomer. After being washed and dried, the resulting core was dipped into a sufficiently mixed and defoamed silicone elastomer of a two-liquid RTV type (SE1740, available from Toray-Daw) which has a refractive index of 1.403. After a cladding was thus dip-coated, the resulting assembly was cured. There was thus obtained an optical fiber having a diameter of about 1 mm and a numerical aperture ("NA") of 0.28. "Numerical aperture" as used herein is given by the following formula:

$$NA = \sqrt{n_{core}^2 - n_{clad}^2}$$

where, $n_{core}$ is the refractive index of a core portion, and $n_{clad}$ is the refractive index of a clad portion. The optical fiber was then dipped into a silicone elastomer of a black two-liquid RTV type (SILPOT™170, available from Dow Corning), and was cured after dip-coating. In this way, an optical fiber for a pressure transducer could be fabricated.

Example 2

Fabrication of an Optical Pressure Transducer

In the structure shown in FIG. 3, the cell 10 was made of polycarbonate, and had a through hole for the optical fiber 80, a pressure sensitive hole 12, a flange for connecting the pressure tube 14, a flange for connecting the flash tube 15, etc. The optical fiber of Example 1 was passed through the through hole, and the sensitivity adjustment screw and the pressure sensitive hole blind screw were fired. A silicone resin containing an inorganic material (Imprint™ available from 3M Co., St. Paul, Minn.) was packed and cured between the optical fiber and the cell. After curing, the optical fiber 80 and the silicone resin swelling out from the cell 10 were cut off, and the blind screw was removed thereby defining a pressure sensitive hole. In this way, the disposable pressure transducer could be fabricated easily.

Example 3

Blood Pressure Transducer

In FIGS. 3 and 4, a blood pressure transducer according to the present invention comprising a sensor head, a monitor unit, a catheter, a flash bag and a vinyl tube is shown. The outside of the sensor head was made of a metal thereby providing electromagnetic shielding, and its top could be opened and closed. A light source unit 9 consisting of a light emitting diode and a monitor sensor, a pressure transducer 8, an optical sensor unit 7 and a connector constituted the sensor head. After the optical sensor unit was inserted into the light source unit, the pressure transducer was then inserted. The vinyl tube 6 was fitted to the pressure tube connection flange 14, and a three-way valve 16 and a flash bag unit were fitted to the flash flange 15.

In this case, the flash bag unit is a pressurization type, and it applies pressure to the physiological saline (to which a heparine, i.e., an anti-clot agent, is added), and supplies the pressurized saline to the pressure transducer 8 through the vinyl tube 6' so that it is possible to prevent the coagulation of the blood.

Further, although detailed explanation will be given in FIGS. 8 and 9, a pressure transducer using reflected light comprises a reflection plate fitted to the end of the pressure transducer 8, and a light measuring unit connected to the other end of the pressure transducer. Further, the pressure tube is connected to the optical fiber at an intermediate part thereof.

Figure 5A:
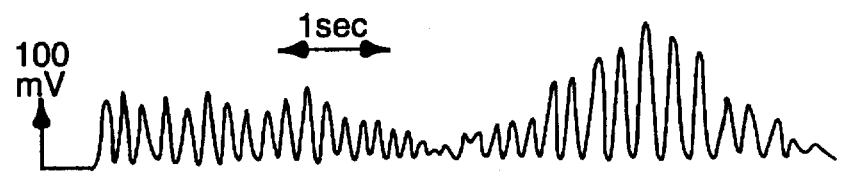
FIGS. 5a and b show response examples of the blood pressure transducer of the present invention.
Figure 5B:
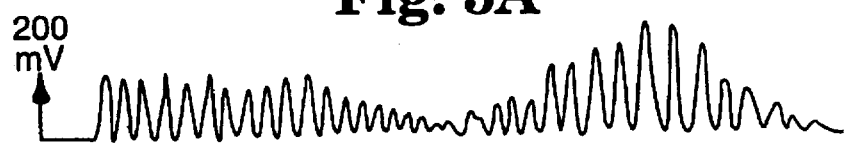

FIGS. 5(A) and 5(B) show examples of responding waveforms when the blood pressure transducer of the present invention was fitted to a calibration pressure generator. The waveform (A) represents the response of the blood pressure transducer and the waveform (B) represents the response of the pressure generator. As can be understood clearly by comparing the waveforms (A) and (B) with each other, there is obtained substantially the same waveform. The pressure sensitivity was about 1.0 mV/mmHg. This sensitivity could be changed by means of the sensitivity adjustment screw of the transducer and by varying the light intensity.

Figure 6:
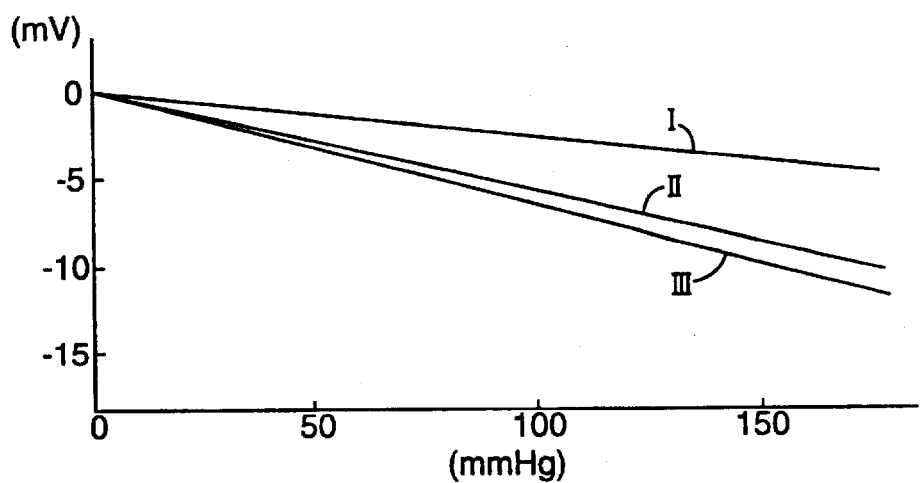
FIG. 6 is a graph showing the effect of the present invention.
Figure 7:
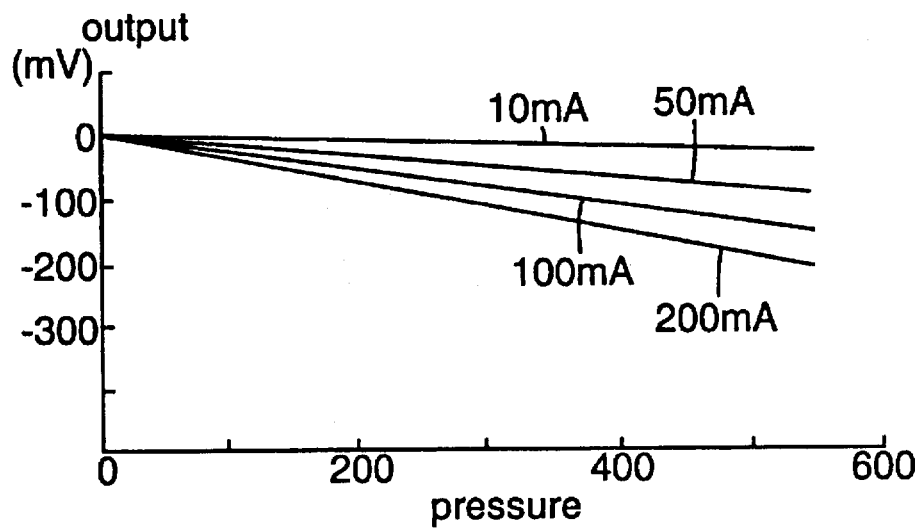
FIG. 7 is a graph showing the effect of the present invention.
Figure 10:
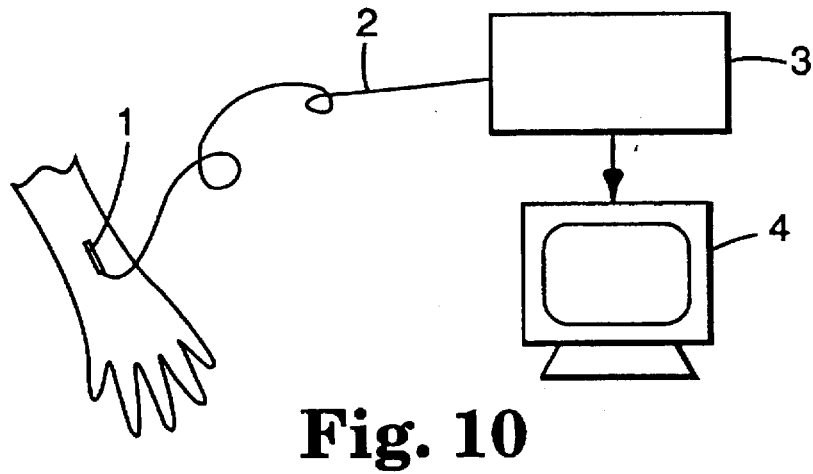
FIG. 10 is an explanatory view of a conventional system.
Figure 11:
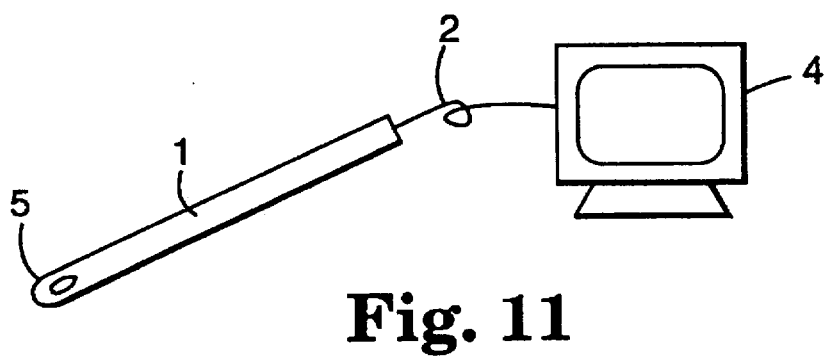
FIG. 11 is an explanatory view of a conventional system.

FIGS. 6 and 7 are graphs useful for explaining the effect of the present invention. FIG. 6 illustrates the effect of the sensitivity adjustment screw and FIG. 7 illustrates the effect of varying the light emission intensity of the LED light source. In FIG. 6, the ordinate represents the sensitivity (mV) of the optical sensor and the abscissa represents the pressure of the solution inside the vinyl tube. Straight lines I, II and III represent the cases where the sensitivity adjustment screw was turned ¾, ½ and ¼ revolutions, respectively. The sensitivity of the optical fiber can thereby be adjusted and variance from other sensors could be eliminated by turning the sensitivity adjustment screw in this way. The ordinate in FIG. 7 represents the sensitivity of the optical sensor and the abscissa represents the pressure Of the solution inside the vinyl tube. The graph represents the relation between the output voltage and the pressure when the current caused to flow through the LED was changed to 10, 50, 100 and 200 (mA), respectively. In this way, the sensitivity could be adjusted by changing the LED current. This blood pressure transducer exhibited a linear relationship over a range of more than 300 mmHg, and the response to the heart rate was at least 500 times/min.

Figure 9:
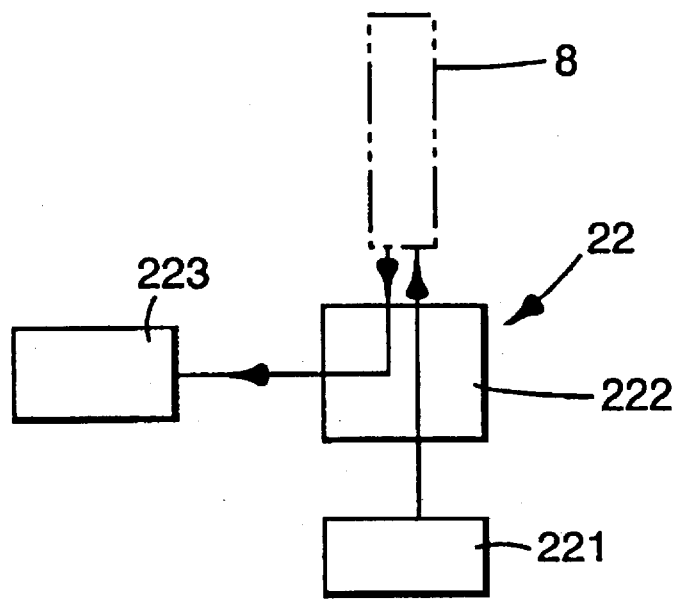
FIG. 9 is a detailed structural view of the light measuring unit shown in FIG. 8.

FIGS. 8 and 9 are structural views of an invasive direct blood pressure transducer according to another embodiment of the present invention. In FIG. 8, reference number 21 denotes a flash bag, 22 a light measuring unit, and 23 a light reflection plate. The light measuring unit 22 is formed by a light source 221, a light splitter 222 and an optical sensor 223 as shown in FIG. 9. In this structure, the light from the light source 221 of the light measuring unit 22 is input to the optical fiber 80 through the light splitter (i.e., beam splitter), and sent into the optical fiber 80 to which the vinyl tube 6 is connected. All light passing through the optical fiber 80 is reflected by the light reflection plate 23 which is fitted to the other end of the optical fiber 80.

The reflection light from the light reflection plate 23 passes through the optical fiber 80 again, changes the light path at a right angle to an incident path by using a half-mirror of the light splitter 23 so as to split a part of the reflection light, and the reflection light is detected by the optical sensor 223 in the light measuring unit 22. Accordingly, the optical sensor 223 detects the intensity of the reflection light. Further, this intensity of the reflection light is converted to the blood pressure to display it on the monitor 4.

In this embodiment, as explained above, the light splitter 222 is provided for sending the reflection light to the optical sensor 223 by using the half mirror. As another example, the beam splitter, a light directional coupler, etc., are usable for the light splitter 222.

In the optical fiber 8, first, the intensity of the incident light from the light source 9 is changed in response to the change of the blood pressure at the pressure sensitive hole 12. Next, the attenuated light is reflected by the reflection plate 23 and is changed again in response to the change of the blood pressure at the same portion 12. Accordingly, since the intensity of the light is twice changed within the optical fiber 80 it is possible to obtain a larger change of the intensity of the light than obtained in the first embodiment in which only the incident light is utilized.

Still further, as explained above, the reflection plate 23 is provided for reflecting the light from the light source 221 through the optical fiber 80. Suitable reflection plates include: a metal plate, a plastic plate, a glass plate, a metal evaporated film, etc.

As explained above, since the light source, the optical sensor and the light splitter are integrated within the light measuring unit, it is possible to achieve the simplified structure.

Various modifications and alterations of this invention will be apparent to those skilled in the art without departing from the scope and spirit of this invention, and it should be understood that this invention is not limited to the illustrative embodiments set forth herein.

I claim:

1. A blood pressure transducer system, comprising:
a catheter (1a) having a first end and a second end,
a pressure tube (6) connected to one of the ends of said catheter (1a) wherein said pressure tube (6) and said catheter (1a) are in fluid communication, and
a pressure transducer (8) connected to an end of said pressure tube (6), wherein said pressure transducer (8) comprises an optical fiber (80) made of a transparent elastomer and having a deformable side surface, a first end and a second end, wherein said pressure transducer (8) comprises a light source (9; 221) and an optical sensor (7; 223), wherein said pressure tube (6) is connected to said optical fiber (80) at an intermediate part of said optical fiber (80), and wherein said optical sensor (7; 223) is capable of detecting the change of the intensity of the light of said light source (9; 221) resulting from the change of a transmission factor of the optical fiber in response to the change of pressure exerted through said pressure tube (6) on the deformable side surface of said optical fiber (80).

2. A pressure transducer system according to claim 1, wherein said light source (9) is arranged to introduce the light at one of the ends of said optical fiber (80) and that said optical sensor (7) is arranged to receive the light transmitted through said optical fiber (80) and output from the other end of said optical fiber (80).

3. A pressure transducer system according to claim 1, wherein said light source (221) and said optical sensor (223) both are arranged so as to introduce light in said optical fiber (80) into and, respectively, to receive the light transmitted through said optical fiber (80) from the same end of said optical fiber (80), and that said pressure transducer (8) further comprises a reflector (23) at the other end of said optical fiber (80).

4. A pressure transducer system according to claim 3, wherein said pressure transducer (8) is equipped with a light measuring unit (22) including a light source (221), an optical sensor (223) having a first end and a second end and a light splitter (222) at one of the ends thereof and with a reflection means (23) at the other end thereof for reflecting a light from said light source (221), said light is allowed to be incident from said light source (221) through said light splitter (222), and said optical sensor (223) detects the change of a light intensity of a reflection light reflected by said reflection means (23) resulting from the change of a transmission factor of said optical fiber (80) in response to the change of pressure exerted through said pressure tube (6) on the deformable side surface of said optical fiber (80).

5. A pressure transducer system according to claim 1, wherein said optical fiber (80) comprises a core portion (81) made of a transparent elastomer having a high refractive index, and a cladding portion (82) made of a transparent elastomer having a low reflective index.

6. A pressure transducer system according to claim 5, wherein said optical fiber (80) further comprises a jacket portion (83) made of an opaque elastomer.

7. A pressure transducer system according to claim 5, wherein the refractive indices of said high refractive index elastomer and said low refractive index elastomer have a difference of at least 0.02.

8. A pressure transducer system according to claim 1, wherein said optical fiber (80) is disposed in a cell (10) and is held in place by means of a packing material (11) which fixes the optical fiber (80) to the cell (10), and that said cell (10) comprises a flange portion (14) for connecting said pressure tube (6) thereto.

9. A pressure transducer system according to claim 8, wherein said cell (10) further comprises a sensitivity adjustment screw (13) for adjusting the variance of sensitivity of said optical fiber (80).

10. A pressure transducer system according to claim 1, wherein said transparent elastomer is selected from the group consisting of silicone elastomers, acrylate elastomers, fluorocarbon elastomers, vinyl chloride elastomers, and ethylene propylene elastomers.

11. A pressure transducer, comprising:

an optical fiber (80) made of a transparent elastomer and having a deformable side surface, a first end and a second end, a light source (9; 221), an optical sensor (7; 223), and a means for connecting a pressure tube (6) at an intermediate part of said optical fiber (80), wherein a change of an applied pressure on the deformable side surface of the optical fiber causes a change of a transmission factor of the optical fiber and a correlatable change of an output signal from said optical sensor (7: 223), wherein the optical fiber (80) is disposed in a cell (10) and is held in place by a packing material (11) which frees the optical fiber (80) to the cell (10), and that the cell (10) comprises a flange portion (14) for connecting the pressure tube (6) thereto.

12. A pressure transducer according to claim 11, wherein said light source (9) is arranged to introduce the light at one of the ends of said optical fiber (80) and that said optical sensor (7) is arranged to receive the light transmitted through said optical fiber (80) and output from the other end of said optical fiber (80).

13. A pressure transducer according to claim 11, wherein said light source (221) and said optical sensor (223) both are arranged so as to introduce light in said optical fiber (80) into and, respectively, to receive the light transmitted through said optical fiber (80) from the same end of said optical fiber (80), and that said pressure transducer (8) further comprises a reflector (23) at the other end of said optical fiber (80).

14. A pressure transducer according to claim 13, wherein there is provided a light measuring unit (22) including a light source (221), an optical sensor (223) having a first end and a second end and a light splitter (222) at one of the ends thereof and with a reflection means (23) at the other end thereof for reflecting a light from said light source (221), said pressure tube (6) is connected to said optical fiber (80) at an intermediate part of said optical fiber (80), said light is allowed to be incident from said light source (221) through said light splitter (222), and said optical sensor (223) detects the change of a light intensity of a reflection light reflected by said reflection means (23) resulting from the change of a transmission factor of said optical fiber (80) in response to the change of pressure exerted through said pressure tube (6) on the deformable side surface of said optical fiber (80).

15. A pressure transducer according to claim 11, wherein said optical fiber (80) comprises a core portion (81) made of a transparent elastomer having a high refractive index, and a cladding portion (82) made of a transparent elastomer having a low reflective index.

16. A pressure transducer according to claim 15, wherein said optical fiber (80) further comprises a jacket portion (83) made of an opaque elastomer.

17. A pressure transducer according to claim 15, wherein the refractive indices of said high refractive index elastomer and said low refractive index elastomer have a difference of at least 0.02.

18. A pressure transducer according to claim 11, wherein said cell (10) further comprises a sensitivity adjustment screw (13) for adjusting the variance of sensitivity of said optical fiber (80).

19. A pressure transducer according to claim 11, wherein said transparent elastomer is selected from the group consisting of silicone elastomers, acrylate elastomers, fluorocarbon elastomers, vinyl chloride elastomers, and ethylene propylene elastomers.

* * * * *

UNITED STATES PATENT AND TRADEMARK OFFICE
CERTIFICATE OF CORRECTION

PATENT NO. : 5,711,291
DATED : January 27, 1998
INVENTOR(S) : Shunsuke Takaki

It is certified that error appears in the above-identified patent and that said Letters Patent is hereby corrected as shown below:

On the title page, please change the name of the inventor from "Sunsuke Takaki" to -- Shunsuke Takaki --.

Col. 5, line 19, "fight" should read -- light --.

Col. 5, line 43, "robe" should read -- tube --.

Col. 19, line 19, "frees" should read -- fixes --.

Signed and Sealed this

Fifteenth Day of June, 1999

Attest:

Q. TODD DICKINSON

Attesting Officer

Acting Commissioner of Patents and Trademarks